(12) United States Patent
Nilsson et al.

(10) Patent No.: US 7,037,342 B2
(45) Date of Patent: May 2, 2006

(54) IMPLANT FOR RECONSTRUCTION OF JOINTS

(75) Inventors: Anders Nilsson, Gothenburg (SE); Bengt Edberg, Gothenburg (SE)

(73) Assignee: Artimplant AB, Vastra Frolunda (SE)

( * ) Notice: Subject to any disclaimer, the term of this patent is extended or adjusted under 35 U.S.C. 154(b) by 0 days.

(21) Appl. No.: 10/250,310

(22) PCT Filed: Jan. 11, 2002

(86) PCT No.: PCT/SE02/00038

§ 371 (c)(1), (2), (4) Date: Dec. 23, 2003

(87) PCT Pub. No.: WO02/054992

PCT Pub. Date: Jul. 18, 2002

(65) Prior Publication Data

US 2004/0093081 A1 May 13, 2004

(30) Foreign Application Priority Data

Jan. 15, 2001 (SE) .................................. 0100127

(51) Int. Cl.
*A61F 2/30* (2006.01)
(52) U.S. Cl. ................. 623/21.15; 623/18.11
(58) Field of Classification Search ............. 623/16.11, 623/18.11, 21.15; 606/151, 154, 155, 60, 606/69, 72, 74, 75, 77
See application file for complete search history.

(56) References Cited

U.S. PATENT DOCUMENTS

| | | | | |
|---|---|---|---|---|
| 2,133,859 A | * | 10/1938 | Hawley | 606/69 |
| 4,502,161 A | * | 3/1985 | Wall | 623/14.12 |
| 4,599,086 A | * | 7/1986 | Doty | 606/61 |
| 4,892,545 A | * | 1/1990 | Day et al. | 623/17.11 |
| 4,916,193 A | * | 4/1990 | Tang et al. | |
| 4,955,915 A | | 9/1990 | Swanson | |
| 6,007,580 A | | 12/1999 | Lehto et al. | |
| 6,017,366 A | | 1/2000 | Berman | |
| 6,093,205 A | * | 7/2000 | McLeod et al. | 623/17.16 |
| 6,113,640 A | | 9/2000 | Tormala et al. | |
| 6,165,217 A | * | 12/2000 | Hayes | 623/11.11 |
| 6,206,883 B1 | * | 3/2001 | Tunc | |
| 6,235,059 B1 | * | 5/2001 | Benezech et al. | 623/17.16 |
| 6,562,073 B1 | * | 5/2003 | Foley | 623/17.11 |

* cited by examiner

*Primary Examiner*—David J. Isabella
(74) *Attorney, Agent, or Firm*—Young & Thompson (57) ABSTRACT

A spacer member (1) is intended to be placed between the ends of the bones which are to be connected, one end of the spacer member being designed to form a joint surface against one of the bone ends (6,7). A joint-stabilizing connection (2,3) is arranged to connect the bones. The spacer member (1) is made of at least one tissue-compatible material.

1 Claim, 8 Drawing Sheets

IMPLANT FOR RECONSTRUCTION OF JOINTS

TECHNICAL FIELD

The present invention relates to an implant for reconstruction of joints, preferably of the hands and feet.

PRIOR ART

Primary wear, arthrosis, of the joints of the hands and feet, for example the carpometacarpal joints of the thumb, is a common condition, especially in middle-aged women. Investigations show that about 12% of all women and 8% of men in their fifties complain of pain at the base of the thumb. The incidence of wear of the big toe, hallux rigidus, is probably even greater. These conditions cause pain at rest and also load-related pain and they reduce mobility. In the hand, this leads to pain in various types of grips and thereby reduces the gripping strength.

In the foot, wear causes pain when walking, with reduced mobility and freedom of movement in the persons affected.

Today, arthrosis of the base of the thumb is initially treated with anti-inflammatory agents, local cortisone injections and various types of supports. At a more developed stage of arthrosis of the base of the thumb, surgical methods are employed. In younger men, and in middle-aged men in work, wear of the joints is preferably treated by an operation stiffening the joint.

Today, in middle-aged and older women, the surgical method employed involves some form of bridging graft with a tendon. However, tendoplasty requires a long period of rehabilitation. The reduction in pain and the increase in mobility are only achieved after 6 to 9 months. Moreover, the persons involved have to live with a permanent loss of strength in the thumb grip.

Various types of prostheses have also been produced, for example for treating arthrosis of the base of the thumb. They are made of titanium, steel, plastic, carbon or silicone. However, they fail after a short time on account of luxation of the joint. It has also been found that when carbon is used, the carbon fibre structure breaks down mechanically over time and the carbon fibre fragments tend to migrate within the body. U.S. Pat. No. 4,411,027 proposes surrounding the carbon fibre structure with a shell of a bioabsorbable polymer for the purpose of protecting the structure from external mechanical action and keeping the fragments in place, at least in the early stage of healing. However, it has been found that carbon fibre fragments from the prosthesis still migrate within the body.

SE-B-457,962 describes an implantable prosthesis for completely or partially replacing a tendon, a ligament or a cruciate ligament. U.S. Pat. No. 6,007,580 further describes a prosthesis made of a biodegradable material, which prosthesis is intended to connect two bones.

However, no suitable implant for reconstruction of joints has hitherto been proposed. Preconditions for such an implant to be able to function well are, first, that it must have properties, such as the requisite strength and mobility, allowing it to replace the functions of the damaged joint, and, second, that it is biocompatible, i.e. that the body is not poisoned or otherwise harmed by the implant. Joints are particularly complicated since they involve joint capsules, ligaments, cartilage and synovial fluid in order to permit natural joint movements.

It has been stated above that joint damage at the base of the thumb is extremely common and represents a major problem and causes suffering and impaired function in those concerned.

Another common problem is hallux rigidus, which is a form of arthrosis of the base of the big toe and which mainly affects men and entails restricted mobility of the metatarsophalangeal joint of the big toe. This means that the foot cannot be deployed in the normal way when walking, and that the person affected suffers pain when walking and an altered gait pattern with loss of speed.

The abovementioned method with a bridging tendon graft means, in the case of treating arthrosis of the base of the thumb, that a bone, namely the trapezoid bone, is removed in its entirety, which means that the thumb is shortened by the order of 1 cm and that the short thumb muscles have an altered range of functioning. Moreover, the proximal end of the metacarpal loses its stability. In order to reduce the instability and avoid conflict with the navicular bone, a bridging graft is formed from a tendon. However, the technique does not mean that the metacarpal is completely stable. This, together with the shortening of the thumb, leads to permanent loss of thumb strength both in the key grip and the three-point grip.

As has been mentioned above, the prostheses which have hitherto been produced are not entirely satisfactory either. One reason is that known prostheses do not stabilize the proximal metacarpal, which means that the prosthesis dislocates.

There has therefore long been a need for a solution to the abovementioned problems which would allow satisfactory reconstruction of damaged joints in humans and animals.

The present invention makes available an implant which is of the type set out in the introduction and which completely eliminates the abovementioned problems.

The implant according to the invention is characterized in that least one spacer member is intended to be placed between the ends of the bones which are to be connected, one end of the spacer member being designed to form a joint surface against one of said bone ends, a joint-stabilizing connection is arranged to connect said bones, the spacer member is made of at least one tissue-compatible material, and the joint-stabilizing connection is intended, upon use of the implant, to extend in the longitudinal direction across the joint and in and over at least one side of the two bones which are connected by the joint.

Since the implant comprises a spacer member, direct contact between adjacent bones is avoided, and thus also the occurrence of pain caused by bone rubbing against bone.

By means of the arrangement of said spacer member and a joint-stabilizing connection it is possible to ensure that during the period of growth of new tissue the implant has the correct form and also appropriate strength and mobility.

According to one embodiment of the invention the material is porous, entirely or partly. This, in combination with a pore size permitting ingrowth of new biological tissue means that the implant according to the invention substantially recreates a functioning joint.

According to one preferred embodiment, the spacer member and the joint stabilizing connection are made of degradable material.

According to a further embodiment the joint-stabilizing connection is made in one piece with the spacer member.

According to one embodiment the degradable material consists of polyurethane urea.

According to another embodiment the degradable material consists of poly-L-lactide.

According to a further embodiment the degradable material consists of polydiaxone (PDS).

According to another embodiment the degradable material consists of poly-β-hydroxybutyrate (PHB).

According to another embodiment the degradable material consists of chitin or chitosan or polysaccharide.

According to a further embodiment the degradable material consists of collagen or protein.

According to a further embodiment the material consists of polyuretan.

According to a further embodiment the material consists of silicone.

According to a further embodiment the material consists of polyethylene terephtalate (PET).

According to another embodiment the inventiontion is characterized in that the implant in its entirety in cross-section mainly has the form of a T, where the stem is said spacer member.

According to one embodiment the invention is characterized in that the spacer member includes a film-like element which is intended to serve as said joint surface.

One embodiment of the invention is characterized in that the spacer member comprises a degradable and tissue-compatible material in the form of foam, fibre or thread, which material is cast, knitted or woven or in some other way formed to give the desired three-dimensional structure.

According to one embodiment, said connection consists of flexible thread-like elements.

According to one embodiment, the invention is characterized in that the joint-stabilizing connection consists of flexible thread-like elements, that said thread-like elements have at least one portion on both sides of the centre line of the two bones, that opposite ends of each of said portions are anchored in the respective bone, and that said portions span the joint and are designed to prevent mutual pivoting of the bones in the lateral direction.

According to a further embodiment, the invention is characterized in that said thread-like elements comprise two portions which each connect the two bones, and that said portions are designed to intersect each other across the joint, as a result of which movements in more than one plane are permitted. When an implant according to this embodiment is arranged for reconstruction of a joint at the base of the thumb, the thumb can be moved in a more natural way during the healing process, which in turn means that growth of new tissue is stimulated, permitting an improved joint function for the thumb.

Further preferred embodiments are set out in the attached patent claims.

The invention will be described in more detail below with reference to illustrative embodiments which are shown in the attached drawing, where.

Figure 1:
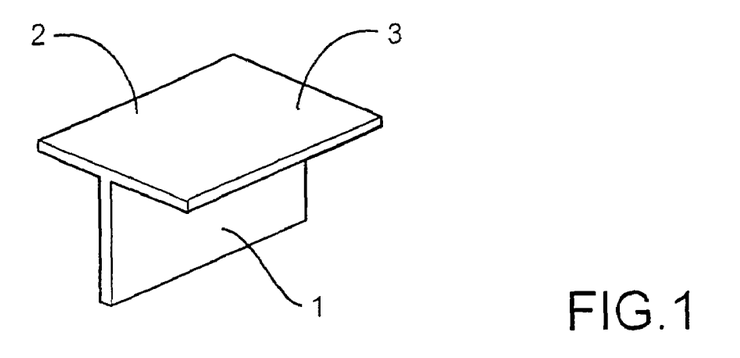
FIG. 1 shows a perspective diagrammatic view of a first illustrative embodiment of an implant according to the invention.

The implant in the illustrative embodiment according to FIG. 1 has a T-shaped cross section with a spacer member 1 and two connection branches 2, 3 which, during use of the implant, are intended to form a joint-stabilizing connection. In the illustrative embodiment shown, the implant is cast in one piece. Suitable materials for the implant are polymers comprising urethane groups with hydrolyzable ester groups or polymers comprising urea and urethane groups with ester links which are hydrolyzable. A suitable starting material for the implant is linear block polymers comprising urea and urethane groups with hydrolyzable ester groups. Material of this type is described in Swedish Patent 505,703. The material according to this publication can be cast into forms of the type shown in FIG. 1 or spun into fibres which are then knitted or woven and shaped to give the desired finished product. Another suitable material is a network polymer which essentially lacks urea groups. Material of this type is described in Swedish Patent 510,868. Implants made of said materials can also be formed by a combination of casting and knitting or weaving. For example, a spacer member can be formed by casting the polymer in question on a reinforcement of the same material, which reinforcement can be designed as a hose or the like and intended to be engaged on a bone end. By choosing their structure and the molecular chains involved, and by adding various substances, the materials of said types described in said Swedish Patents 505,073 and 510,868 can be controlled with respect to their mechanical properties and also with respect to their degradation time.

The implant according to the invention is intended to be used in the reconstruction of damaged joints in humans and animals. The geometric design and the mechanical properties are chosen in accordance with the intended purpose. The implant will temporarily replace the damaged joint and the time of degradation of the implant must exceed the time for formation of cartilage-like tissue in the spacer member and joint-stabilizing connective tissue for forming a joint-stabilizing connection. The implant is designed so that, during the rehabilitation period, it fulfils the intended joint functions with sufficient strength and mobility. This, in combination with the fact that the spacer member is porous and has a pore size permitting ingrowth of new biological tissue, means, as has been mentioned above, that the implant according to the invention stimulates recreation of a functioning joint, at the same time as the implant is degraded. Material according to SE 505,703 and SE 510,868 is broken down by hydrolysis and thereafter eliminated from the body.

Figure 2:
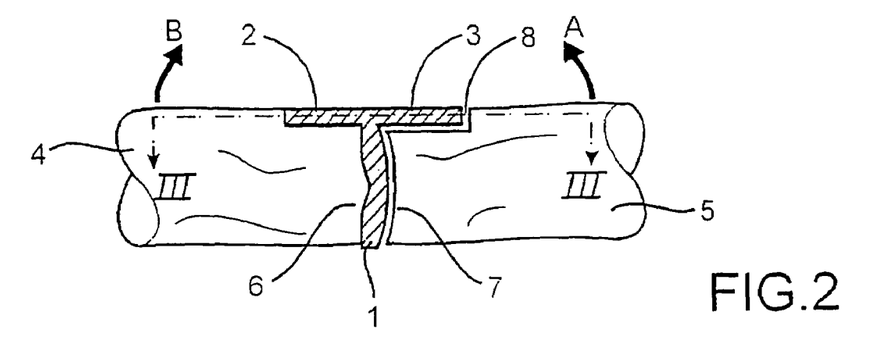
FIG. 2 shows a cross section through an implant according to FIG. 1 arranged in a joint between two bones.

In FIG. 2, the implant according to FIG. 1 has been arranged in a damaged joint, for example a finger joint, between two bones 4, 5. The spacer member 1 is arranged between the bone ends 6, 7 of the respective bones, by which means direct contact between adjacent bone ends is prevented and pain caused by bone rubbing against bone is avoided. Before the implant has been fitted, recesses 8 have been formed in the bones 4, 5 and are intended to accommodate the joint-stabilizing connection formed by the branches 2, 3. The bone end 7 serves as an articular socket and the bone 5, in the position shown in FIG. 2, is pivotable in the direction of the arrow A about the temporary joint surface which is formed by the spacer member 1. The implant is flexible but substantially non-stretchable during normal use, i.e. under the forces which occur when a finger joint is bent in a natural manner. The bone 5 can thus be bent from the position shown in FIG. 2 by the order of magnitude of 90° and back, but not clockwise from the position shown in FIG. 2. The opposite surface of the spacer member is in contact with a bone end 6 serving as an articular head on the bone 4, and the bone 4 can pivot correspondingly in relation to the bone 5 in the direction of the arrow B. The spacer member, like the rest of the implant, is porous with a pore size which permits ingrowth of new cartilage tissue for continuous re-formation of a permanent joint. The pore size also permits ingrowth of joint-stabilizing connective tissue in the branches 2, 3 of the implant, for continuous replacement of the temporary joint-stabilizing connection. Reformation of new cartilage tissue for the spacer body takes something in the region of 1½ to 2 years and the total degradation time for the temporary spacer body must therefore exceed this period of time. The connective tissue which replaces the temporary connection is re-formed in a shorter time than cartilage tissue, and it takes something in the region of six months to 1½ years for connective tissue to completely re-form.

Figure 3:
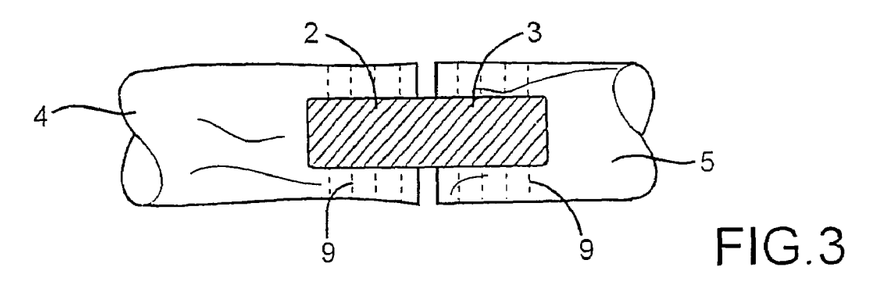
FIG. 3 shows a section along the line III—III in FIG. 2.

In the illustrative embodiment shown in FIGS. 2 and 3, the implant has been secured in the bones 4, 5 by means of suture threads 9 which, as is shown in FIG. 3, connect the branches 2, 3 of the implant to the respective bones.

Figure 4:
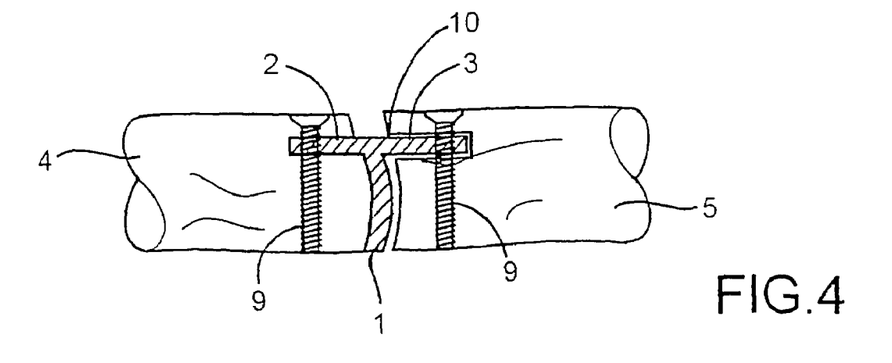
FIG. 4 shows a cross section of an implant according to FIG. 1 arranged in a joint between two bones, in a modified way compared to FIG. 2.

In the illustrative embodiment shown in FIG. 4, details corresponding to similar ones in the illustrative embodiment according to FIGS. 2 and 3 have been provided with the same reference numbers. Compared to FIGS. 2 and 3, FIG. 4 shows an alternative means of securing the implant according to FIG. 1. Instead of the recess 8, grooves 10 for the branches 2, 3 have been formed in the bones 4 and 5, as can be seen from FIG. 4. These branches, which form a joint-stabilizing connection, have been secured in the bones 4 and 5, respectively, by means of continuous screws 9'. In the method according to FIG. 4, an uninterrupted hard outer bone surface is obtained on both the bones 4 and 5.

Figure 5:
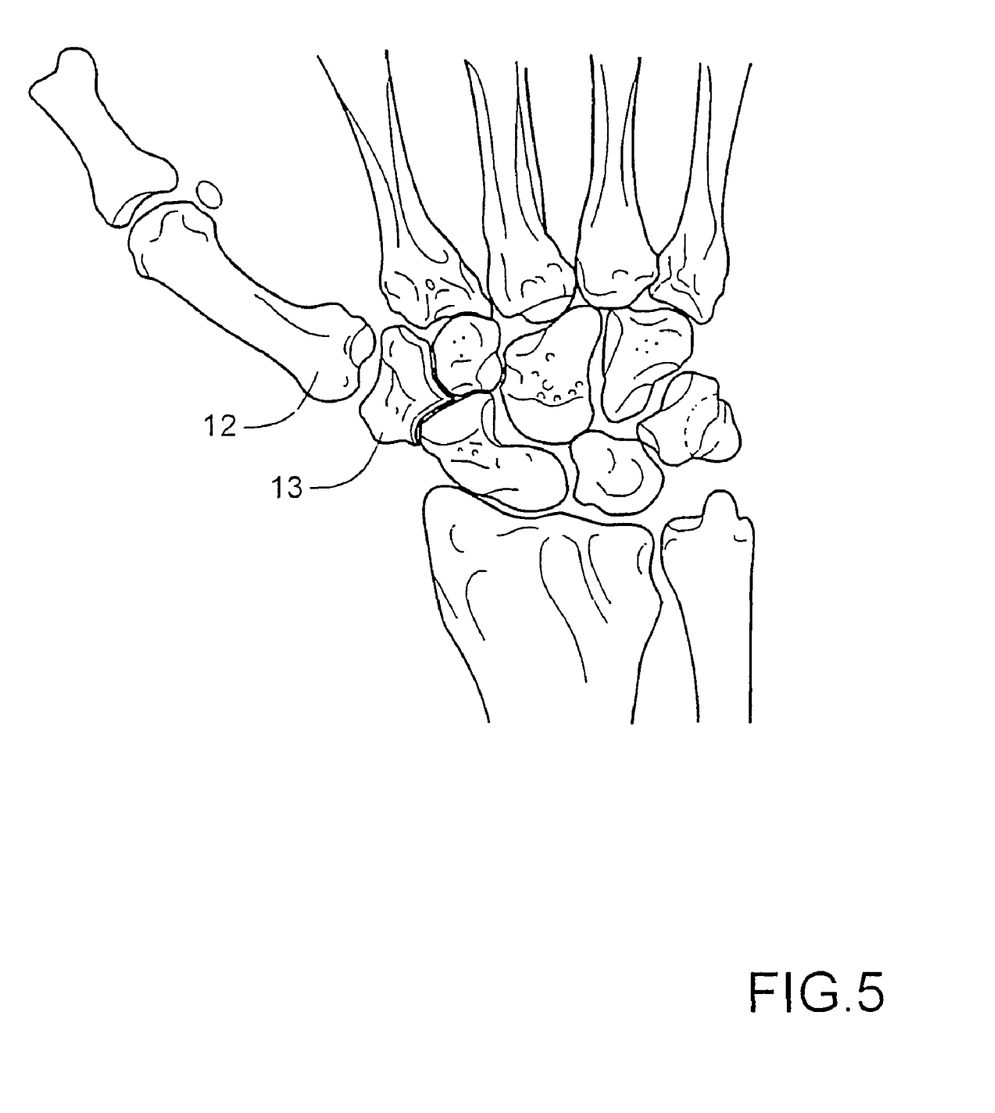
FIG. 5 shows a perspective view of the bones in a hand and wrist.

As was stated in the introduction, primary wear, for example in the carpometacarpal joints of the thumb, is a common type of condition which causes degradation and attrition of joint cartilage. FIG. 5 shows the bones of the hand from above, i.e. the back of the hand. In the drawing, the 1st metacarpal has been indicated by 12 and the trapezoid bone by 13. Said joint condition, namely arthrosis of the base of the thumb, occurs in the joint between the 1st metacarpal 12 and the trapezoid bone 13.

Figure 6:
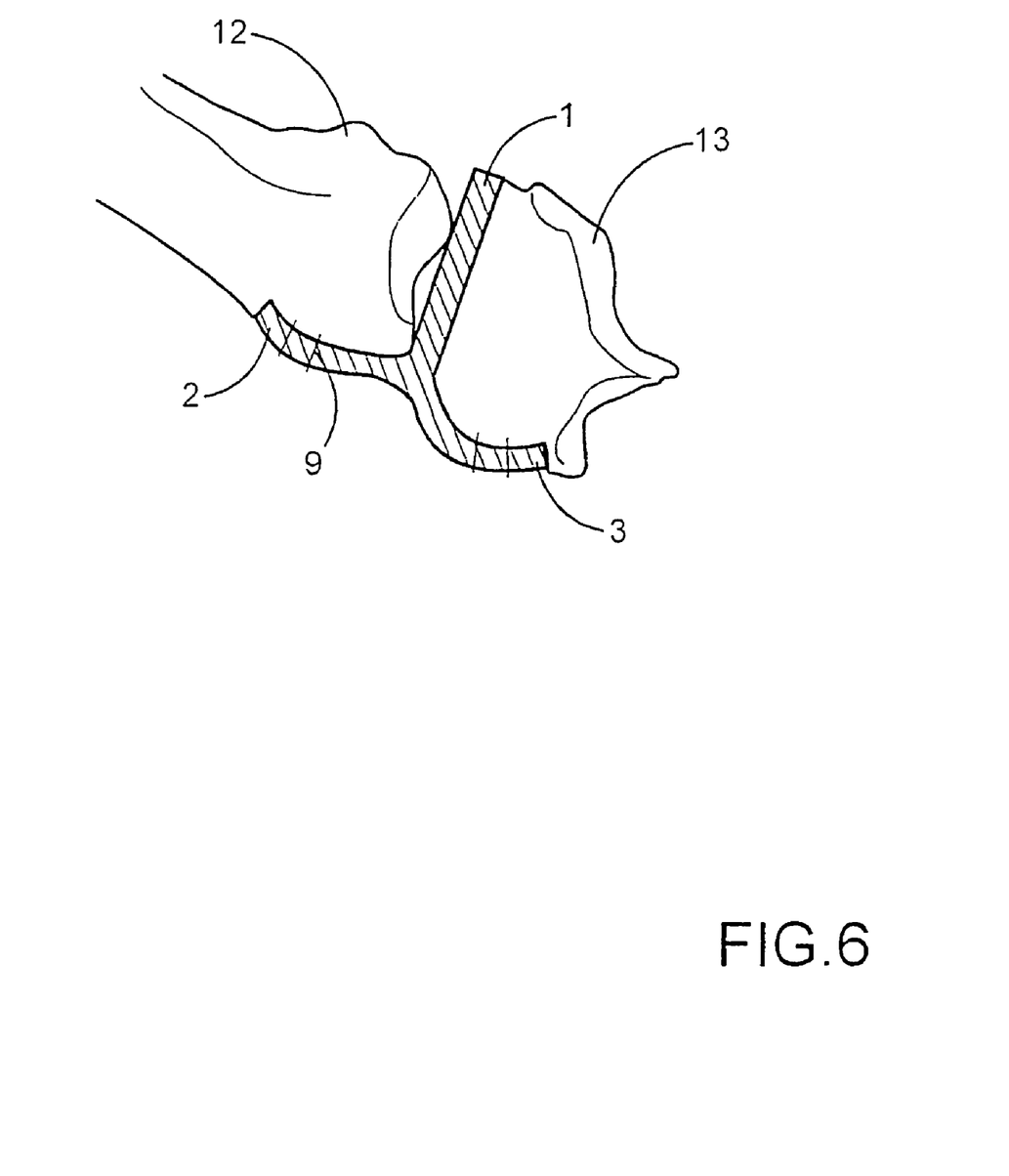
FIG. 6 shows a portion of the hand shown in FIG. 5, with an implant according to FIG. 1 arranged in a joint at the base of the thumb.

FIG. 6 shows how an implant according to FIG. 1 can be arranged between said bones 12 and 13. In the example shown, a worn portion of the trapezoid bone 13 has been removed and the spacer member 1 has been arranged between this sectioned bone and the 1st metacarpal 12. The spacer member 1 bears tightly on the surface of the sectioned bone. The branches 2, 3 have been connected by means of suture threads 9 to the respective bones 12 and 13 in order to form a joint-stabilizing connection at the base of the thumb.

Figure 7:
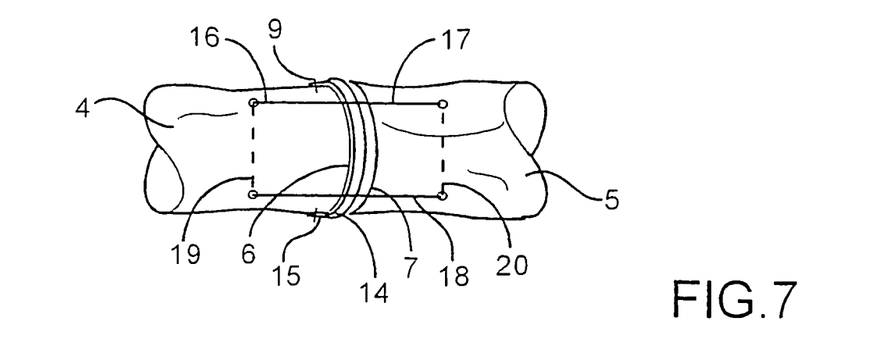
FIG. 7 shows a second illustrative embodiment of an implant according to the invention arranged in a joint between two bones.
Figure 8:
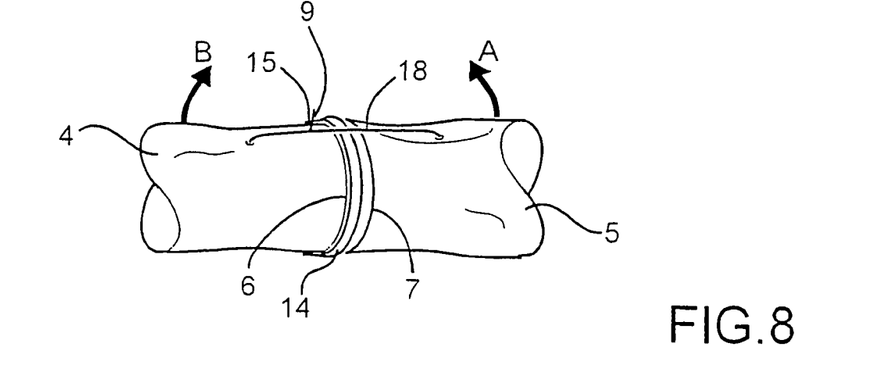
FIG. 8 shows a side view of the implant and bones according to FIG. 7.
Figure 13:
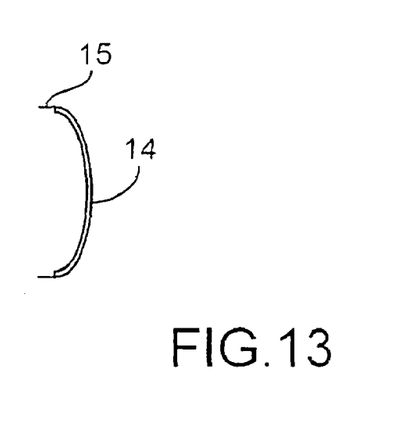
FIGS. 13 and 14 show two sizes of spacer bodies which are included in the implant according to the illustrative embodiments in FIGS. 7–12 and which are intended to form articular heads in a joint.
Figure 14:
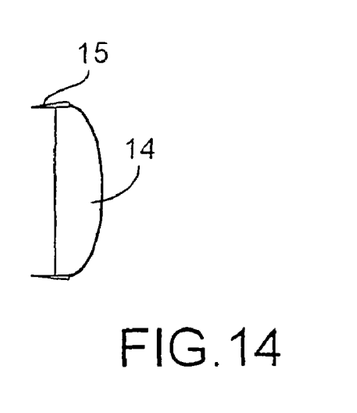

FIGS. 7 and 8 show a second illustrative embodiment of an implant according to the invention arranged in a joint between two bones 4 and 5, for example in a finger or a toe. A spacer member 14 is arranged in the joint between the two bones. This spacer member 14 is preferably made of the same material as the implant according to the first embodiment. The spacer member 14 of the type included in the implant according to FIGS. 7 and 8 is shown separately in FIGS. 13 and 14. A spacer member of this type can be produced in different sizes and thicknesses. FIG. 13 shows a very thin spacer member 14, and FIG. 14 shows a very thick spacer member 14. For joints in the hands and feet, the necessary thickness of the spacer member varies in the range of 0.5 to 7 mm. For joints in animals, the thickness of spacer bodies of the type shown in FIGS. 13 and 14 can preferably vary within wider limits. The spacer bodies 14 are provided with securing portions 15 which are expediently made of the same material as the rest of the spacer body. The securing portions 15 according to FIG. 13 are made for example as woven or knitted ligaments. Alternatively, the securing portions can consist of suture threads or some other degradable, preferably bio-erodable material. The securing portions 15 are used for anchoring the spacer member 14 on one of the bones. FIG. 7 shows diagrammatically how the securing portions 15 have been connected to the bone 4 by means of suture threads 9. The implant according to FIGS. 7 and 8 includes a flexible thread-like element 16 which is intended to serve as a temporary joint-stabilizing connection. As can be seen from FIGS. 7 and 8, the thread-like element has a portion 17, 18 on both sides of the centre line of the two bones, which portions extend in the longitudinal direction of the bone and over the joint. In this illustrative embodiment, the thread-like element is made in one piece and extends with portions 19 and 20 through holes in the bones 4, 5, respectively.

As in the embodiment according to FIGS. 2 and 3, the bones 5 and 4 can be bent from the position shown in FIG. 8 in the direction of the arrows A and B, respectively. The thread-like element is made of a degradable, preferably bio-erodable material, preferably of a linear block polymer of the type which has been described above, and has further been designed with mechanical properties similar to a natural ligament within its natural range of movement. This means that the thread-like element has, at least within a normal ligament's range of functioning, similar mechanical properties but that beyond this range of functioning it may be overdimensioned compared to a normal ligament. The thread-like element 16 is flexible but substantially non-stretchable, which means that the bones 4, 5 in the position shown in FIG. 8 cannot be bent about the joint in the direction counter to the arrows A and B, respectively.

Figure 9:
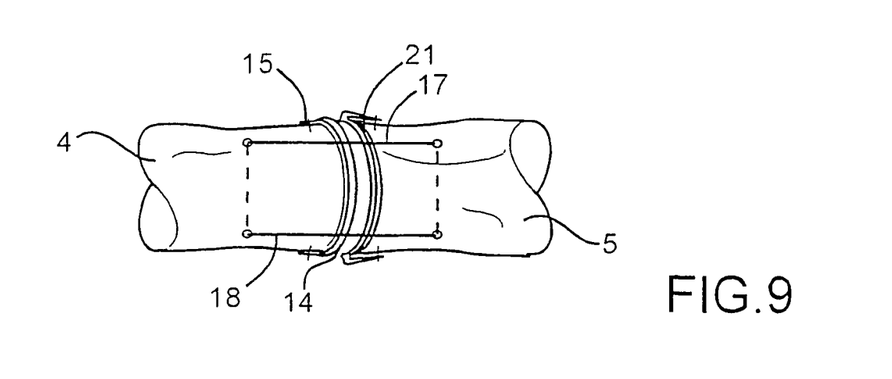
FIG. 9 shows a view similar to FIG. 7 with an implant according to a third illustrative embodiment, slightly modified in relation to the embodiment according to FIG. 7.
Figure 10:
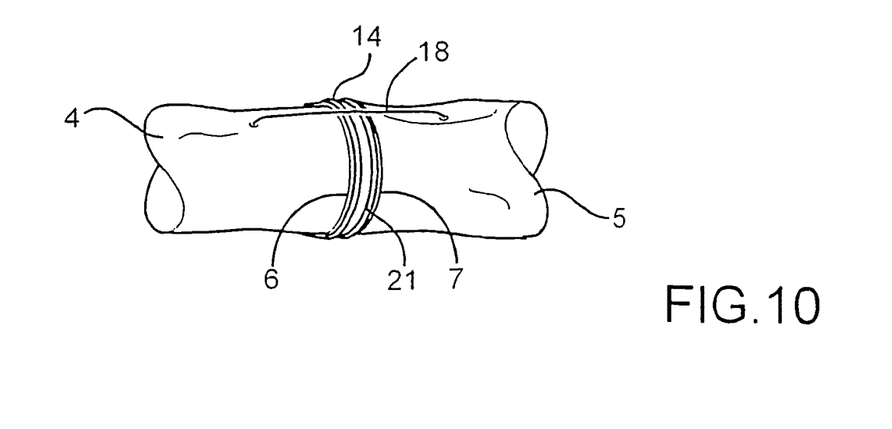
FIG. 10 shows a side view of the implant and bones according to FIG. 9.

A third illustrative embodiment according to FIGS. 9 and 10 corresponds to a large extent to the embodiment according to FIGS. 7 and 8. Corresponding details in said embodiments have been provided with the same reference numbers. What distinguishes the implant according to FIGS. 9 and 10 from the embodiment described in connection with FIGS. 7 and 8 is that a further spacer member 21 has been arranged against the bone end 7 of the bone 5. Spacer members of this type and designed as an articular socket are shown separately in FIGS. 15 and 16. In the same way as has been described in connection with FIGS. 13 and 14, the thickness of the spacer member can be varied within the same limits. Moreover, the spacer members designed as articular sockets are provided with securing members 15 which are intended to anchor the spacer body 21 on the bone 5 by means of suture threads 9, as shown in FIGS. 7 and 8.

Figure 11:
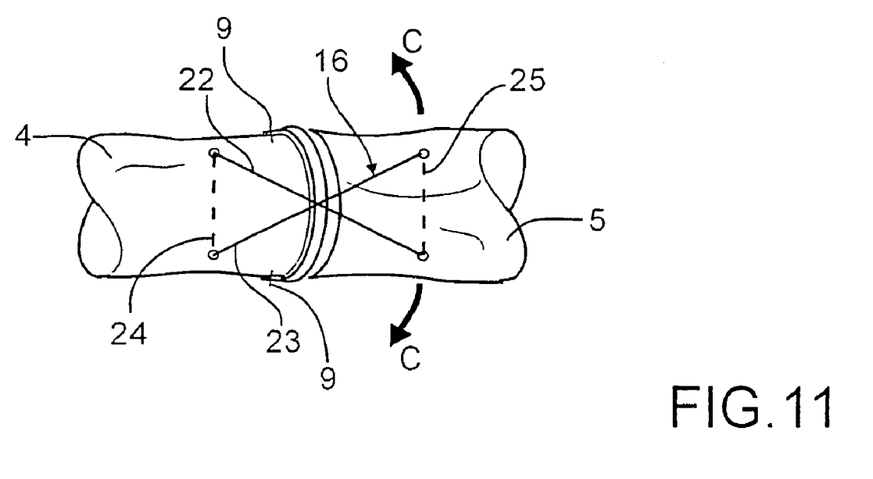
FIG. 11 shows a fourth illustrative embodiment of an implant according to the invention arranged in a joint between two bones.
Figure 12:
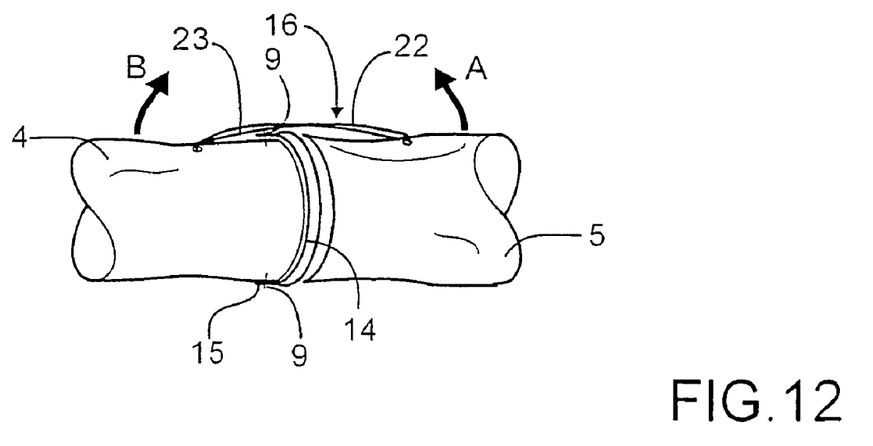
FIG. 12 shows a side view of the illustrative embodiment according to FIG. 11.

FIGS. 11 and 12 show a fourth illustrative embodiment of an implant according to the invention. This fourth embodiment differs from the illustrative embodiment shown in FIGS. 7 and 8 only with respect to the thread-like element. This has been arranged with thread portions 22, 23 intersecting across the joint between two bones 4, 5, as can be seen from FIGS. 11 and 12. The thread-like element is made in one piece 16 and has portions 24, 25 which extend through holes in the bones 4 and 5. Since the thread portions 22 and 23 run more freely on one side of the bone compared to the embodiments described in connection with FIGS. 7 to 10, where respective thread portions 17 and 18 run on both sides of the longitudinal centre line of the bones and prevent mutual pivoting of the bones in the lateral direction, the bones 4 and 5 can, in addition to the possibility of pivoting in the direction of the arrows A and B in FIG. 12, also be pivoted in another plane, such as is indicated by the arrows C in FIG. 11.

Figure 17:
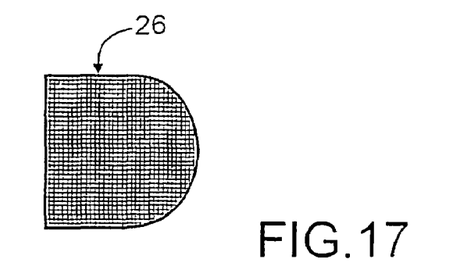
FIGS. 17 and 18 show the structure of a spacer member in an implant according to a fifth embodiment.

FIG. 17 shows a knitted or otherwise formed network structure 26 made of a degradable material, preferably from said linear block polymers according to SE 505,703. Said structure has the shape of a hood and is intended to serve as reinforcement in an implant. The latter is formed by means of a degradable material, preferably in the form of polyurethane with hydrolyzable ester groups, being cast from outside onto the top of the hood. Said material is described in SE 510,868.

Figure 18A:
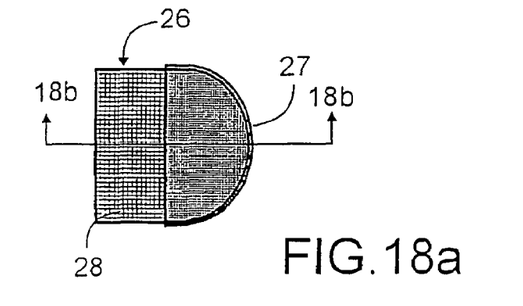
Figure 18B:
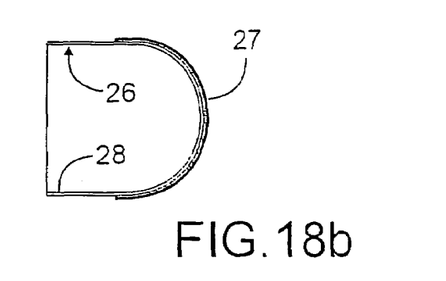

FIG. 18 shows the finished spacer member after casting, intended to serve as an articular head in a joint, for example a finger joint. The cast-on material has been indicated by 27 in FIG. 18. The network structure 26 forms a hose which strengthens the spacer body from the inside, and the network portion 28 protruding from the cast body 27 forms a hose portion which is intended to be engaged on a bone which is to be connected to an adjacent bone via the joint. A further purpose of the network structure, besides that of serving as a strengthening means, is to create a high degree of friction against the bone and facilitate growth therein. The network structure 26 is also stable for sewing in upon fixation to the bone.

Figure 19A:
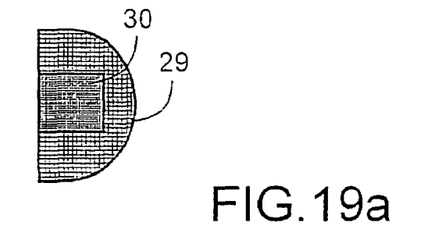
FIGS. 19 and 20 show, in longitudinal section, the structure of a spacer member in an implant according to a sixth embodiment.
Figure 19B:
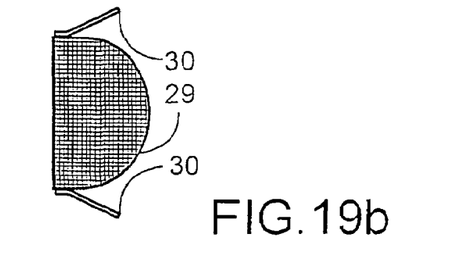

FIG. 19 shows, in a similar way to FIG. 17, a knitted or otherwise formed network structure 29 which is intended to form an outer reinforcement for a spacer member, which is intended to serve as an articular socket, i.e. as a complement to a spacer member of the type which has been described in connection with FIGS. 17 and 18.

The network structure 29 is provided with one or more securing portions 30 which are intended to be secured on the outside of a bone by means of suture thread or the like. The securing portion 30 can go all the way round or be made up of one or more securing portions.

An illustrative embodiment with two securing portions 30 is shown in the drawing.

Figure 20A:
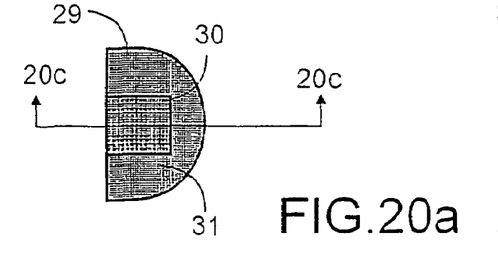
Figure 20B:
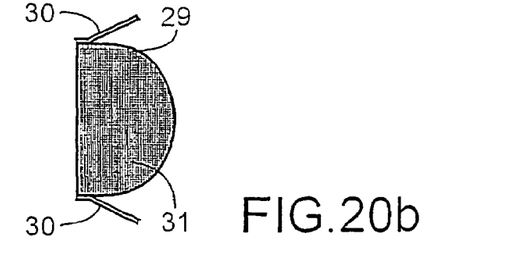
Figure 20C:
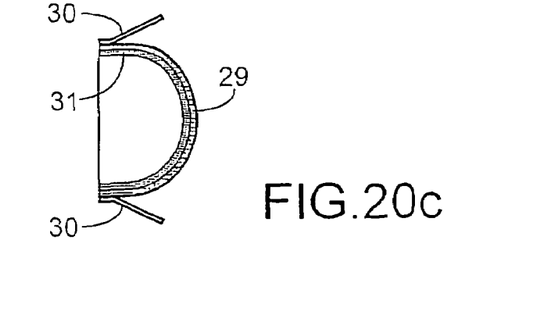

A degradable material, preferably in the form of polyurethanes with hydrolyzable ester groups, is cast onto the inside of the network structure, as can be seen from FIG. 20, for forming an articular socket. The cast-on material has been indicated by 31 in FIG. 20. The purpose of the network structure according to FIG. 20 is the same as has been described in connection with FIG. 18, i.e. to serve as reinforcement in the spacer member, create friction against the bone and facilitate growth in the bone.

Figure 15:
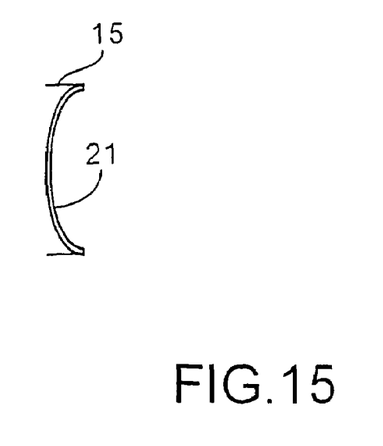
FIGS. 15 and 16 show two sizes of spacer bodies which are included in the implant according to the illustrative embodiments in FIGS. 9 and 10 and which are intended to form articular sockets in a joint.
Figure 16:
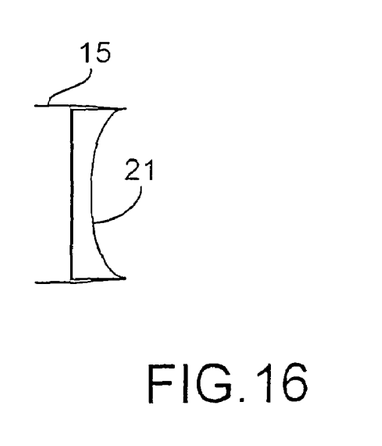

FIGS. 17 to 21 show relatively thin spacer members corresponding to the spacer members shown in FIGS. 13 and 15.

Figure 21A:
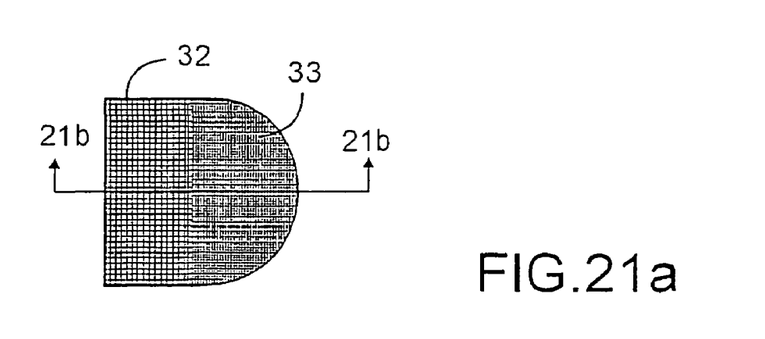
FIGS. 21 and 22 show the structure of a spacer member in an implant according to a seventh embodiment.
Figure 21B:
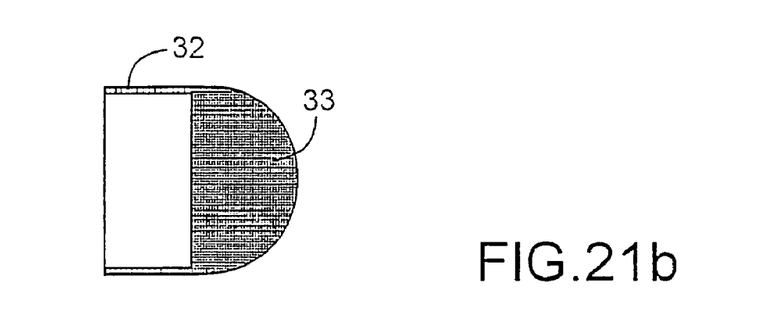

FIGS. 21a and 21b show a knitted or otherwise formed network structure 32 of the type which has been described in connection with FIG. 17 above. The network structure 32 differs from that shown in FIG. 17 in that the top 33 of the structure is condensed and in that the reinforcement in the top 33 has a depth which will substantially correspond to the thickness of the degradable material 34, see FIG. 22, which is cast from the outside and in across the depth of the network structure in the top 33. The cast material 34 like the network structure is expediently made of polyurethanes with hydrolyzable ester groups.

Figure 22A:
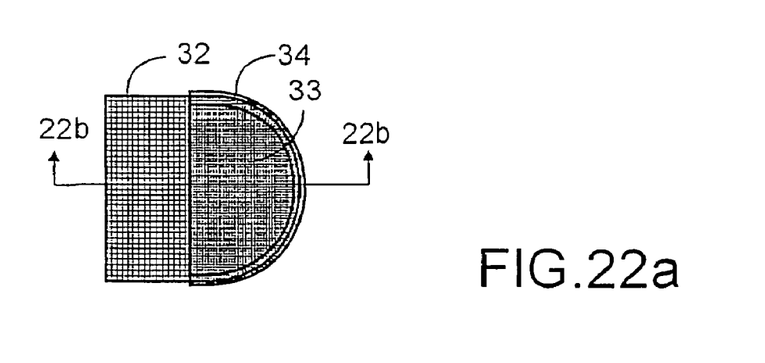
Figure 22B:
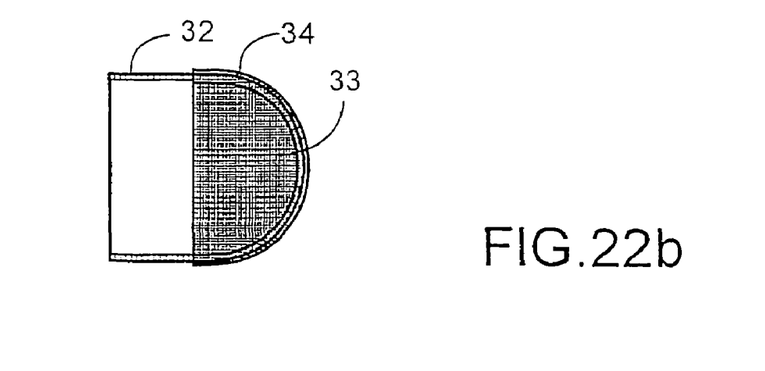

The actual spacer member in the embodiment according to FIG. 22 has a thickness which substantially exceeds the thickness of the spacer member according to FIG. 18. In principle, the difference arises in the same way as the difference in size which has been described in connection with FIGS. 13 and 14 above. The network structure 32 fulfils the same purposes as have been described above in connection with FIGS. 17 to 20.

However, the network structure 32 has a substantial depth at the top 34 and in this area it will serve also as internal reinforcement in the cast-on material. It is important that the spacer member in a joint does not collapse under the pressures which arise during natural use of the joint, and instead the temporary spacer member must hold adjacent bone ends at a distance from each other. It is of course also important that the temporary spacer members are resistant to wear.

The different embodiments of the spacer members shown in FIGS. 17 to 22 are combined with a joint-stabilizing connection, for example in the form of flexible thread-like elements which have been described in connection with FIGS. 7 to 12.

The invention is not limited to the illustrative embodiments described above, and instead it can be modified in a number of ways within the scope of the attached patent claims.

The spacer member, which can consist of a cast or spun and thereafter knitted or woven structure or an otherwise formed structure, can be provided, as has been described above, with strengthening threads of the same material as the rest of the structure or of another degradable and tissue-compatible material.

Said strengthening threads can be arranged to form a reinforcement skeleton which is intended to give the structure stability without locking it. The strengthening threads can for example be arranged in a defined direction in order to afford increased strength in this direction.

The reinforcement skeleton can consist of a shell which surrounds the rest of the structure. In addition to said shell, the reinforcement structure can also comprise strengthening threads in one or more defined directions.

In the above described embodiment have been mentioned suitable examples of materials for a degradable implant.

Further examples of degradable materials for the implant in accordance with the invention are defined in the following patent claims.

The invention is not restricted to implants of degradable materials. Examples of non-degradable materials are silicone and polyethylene terephtalate.

The implant according to the invention can have different forms than have been described above. All corners of the in the figures schematically shown T-shaped implant are preferably rounded.

The implant can be shaped as a plate with integrated fastening members or joint-stabilizing connections. The implant can have a sponge-like shape with integrated stabilizing connections.

Within the scope of protection is an implant arranged such that the shape of the implant is adapted to the anatomic shape when exposed to load.

The joint-stabilizing connection can be designed in a different way than has been described above.

The material of the spacer member can consists of polytetrafluoro ethylene (PTFE). Also the joint-stabilizing connection can be made in the same material. This material is generally known under the trade name TEFLON®.

The invention claimed is:

1. Implant for reconstruction of joints, preferably of the hands and feet, comprising
    at least one spacer member (1) adapted to be placed between the ends of the bones which are to be connected, one end of the spacer member being designed to form a joint surface against one of said bone ends (6, 7),
    a joint-stabilizing connection (2, 3) adapted to connect said bones,
    the spacer member (1) being made of at least one tissue-compatible material,
    the joint-stabilizing connection (2, 3) being adapted, upon use of the implant, to extend in the longitudinal direction across the joint and in over at least one side of the two bones (4, 5) which are connected by the joint,
    the material of the spacer member (1) being at least partly porous,
    the spacer member (1) and the joint-stabilizing connection being made of degradable material,
    the joint-stabilizing connection being made in one piece with the spacer member (1),
    the degradable material being polyurethane urea;
    the spacer member (1) and the joint-stabilizing connection being made entirely of woven fibrous material; and
    the spacer member (1) and the joint-stabilizing connection comprising at least two branches that meet at a dihedral angle.

* * * * *